US005739395A

United States Patent [19]

Bergeron, Jr.

[11] Patent Number: 5,739,395
[45] Date of Patent: Apr. 14, 1998

[54] METHOD FOR SYNTHESIS OF RHIZOFERRIN

[75] Inventor: Raymond J. Bergeron, Jr., Gainesville, Fla.

[73] Assignee: University of Florida Research Foundation, Inc., Gainesville, Fla.

[21] Appl. No.: 783,306

[22] Filed: Jan. 10, 1997

[51] Int. Cl.⁶ .................... C07C 229/24; C07C 229/26; C07C 229/22
[52] U.S. Cl. .................................. 562/565; 562/526
[58] Field of Search ........................ 562/565, 526

[56] References Cited

PUBLICATIONS

Bergeron et al., "Total Synthesis . . . An Iron Chelator", Tetrahedron, vol. 53, No. 2, pp. 427–434, Jan. 1997.
Tschierske et al., "Production . . . Fermentation", Appl. Microbiol. Biotech., vol. 45, No. 5, pp. 664–670, Jun. 1996.
Willaims et al., "Carbanion–Mediated . . Amides", Tetrahedron Letters, vol. 30, No. 4, pp. 451–454, 1989.
Drechsel et al, *Biol. Metals*, vol. 4, "Rhizoferrin–a novel siderophore from the fungus *Rhizopus microsporus* var. *rhizopodiformis*," pp. 238–243 (1991).
Thieken et al, *FEMS Microbiology Letters*, vol. 94, "Rhizoferrin: A complexone type siderophore of the Mucorales and Entomophthorales (Zygomycetes)," pp. 37–42 (1992).

Drechsel et al, *Biol. Metals*, vol. 5, "Stereochemical characterization of rhizoferrin and identification of its dehydration products," pp. 141–148 (1992).

Smith, *Tetrahedron Letters*, vol. 30, No. 3, "Total Synthesis and Absolute Configuration of Rhizobactin, a Structurally Novel Siderophore," pp. 313–316 (1989).

Konetschny–Rapp et al, *Eur. J. Biochem.*, vol. 191, "Staphyloferrin A: a structurally new siderophore from staphylococci," pp. 65–74 (1990).

Bergeron et al, *CRC Handbook of Microbial Iron Chelates*, "Synthesis of Catecholamide and Hydroxamate Siderophores," pp. 271–307 (1991).

Samejima et al, *Chem. Pharm. Bull*, vol. 32, No. 9, "Synthesis of N–Enriched Polyamines," pp. 3428–3435 (1984).

*Primary Examiner*—Gary Geist
*Assistant Examiner*—Rosalynd Keys
*Attorney, Agent, or Firm*—Kerkam, Stowell, Kondracki & Clarke; Dennis P. Clarke

[57] ABSTRACT

A method of synthesizing rhizoferrin and analogues thereof comprising acylating a protected polyamine with a citric acid diester; hydrolyzing the resulting amide to produce an N-protected rhizoferrin or analog thereof; and de-protecting the intermediate to produce rhizoferrin or the analog thereof.

21 Claims, No Drawings

METHOD FOR SYNTHESIS OF RHIZOFERRIN

Research leading to completion and reduction to practice of the invention was supported in part by Grant No. R01DK-49108 awarded by the National Institutes of Health (NIH). The United States Government has certain rights in and to the invention described and claimed herein.

BACKGROUND OF THE INVENTION

1. Field of the Invention

The invention relates to a method for preparing the chelator, rhizoferrin.

2. Description of the Prior Art

Iron is essential for almost all forms of life. However, because of the aqueous insolubility of Fe(OH)$_3$, ($K_{sp}$=2× 10$^{-39}$), the predominant form of the transition metal in the environment, virtually all life forms have developed rather sophisticated iron chelating and transport systems to utilize the metal. Higher animals tend to utilize proteins to transport and assimilate iron.

Microorganisms produce a group of low molecular weight chelators or siderophores [Bergeron, "Synthesis and Solution Structures of Microbial Siderophores," *Chem. Rev.*, Vol. 84, pages 587–602 (1984); Tait, "The Identification and Biosynthesis of Siderochromes Formed by *Micrococcus denitrificans*", *Biochem. J.*, Vol. 146, pages 191–204 (1975); Griffiths et al, "Vibriobactin, a Siderophore from *Vibrio cholerae*," *J. Biol. Chem.*, Vol. 259, pages 383–385 (1984); Aksoy et al, "Hypertransfusion and Iron Chelation in Thalassaemia," page 80, Hans Huber Publishers, Berne (1985); and Bickel et al, "Metabolic products of actinomycetes. Ferrioxamine B," *Helv. Chim. Acta.*, Vol. 43, pages 2129–2138 (1960)] for the purpose of acquiring iron. The metal exists in the biosphere largely in the insoluble ferric state and would be otherwise inaccessible to bacteria without such ligands. Although a large number of siderophores have been identified, they fall largely into two structural classes: the catecholamides and the hydroxamates [Bergeron, supra]. Many of the ligands of both structural types contain polyamine backbones. While the hexacoordinate catecholamides parabactin [Tait, supra] and vibriobactin [Griffiths et al, supra] are predicated on the triamines spermidine and norspermidine, respectively, the hydroxamates are frequently derived from the diamines, putrescine or cadaverine, or from their biochemical precursors, ornithine or lysine [Bergeron, supra]. For example, the siderophores isolated from *Streptomyces pilosus*, desferrioxamines A–I, consist of a group of hydroxamates with either repeating putrescine or cadaverine units in their backbones [Aksoy et al, supra]. The most well known of these chelators, desferrioxamine B (DFO) [Bickel et al, supra], is a linear trihydroxamate ligand which forms a very stable hexacoordinate, octahedral complex [Modell et al, "The Clinical Approach to Thalassaemia," page 217, Grune and Stratton, London (1984)] with iron (III), $K_f$=1× 10$^{30}$ M$^{-1}$. Although DFO binds a number of different +3 cations, e.g., Al (III), Ga (III), Cr (III), it exhibits a high specificity for iron (III). It is not too surprising then that the mesylate salt of desferrioxamine, Desferal®, has been employed in the treatment of several iron overload diseases such as thalassemia [Anderson, "Inorganic Chemistry in Biology and Medicine," Chapter 15, American Chemical Society, Wash., D.C. (1973); and Fisher et al, "Development of an Intravenous Desferrioxamine Mesylate Treatment Protocol for Swine: Monitoring of Desferrioxamine and Metabolites By High-Performance Liquid Chromatography," *Pharmacology*, Vol. 41, pages 263–271 (1990)]. However, the fact that patients must be continuously infused because of the short half-life of the drug in the body has compelled investigators to continue the search for better therapeutic iron chelators.

N$^1$,N$^4$-Bis(1-oxo-3-hydroxy-3,4-dicarboxybutyl) diaminobutane (rhizoferrin) was first isolated from *Rhizopus microsporus* var. *rhizopodiformis*, an organism associated with mucormycosis seen in dialysis patients [Drechsel et al, *Biol. Met.*, Vol. 4, pages 238–243 (1991)], and occurs in several Zygomycetes strains of fungi [Thieken et al, *FEMS Microbiol. Lett.*, Vol. 94, pages 37–42 (1992)]. Like the natural chelators parabactin and DFO, rhizoferrin forms a 1:1 complex with ferric ion [Drechsel et al, *Biol. Met.*, Vol. 5, pages 141–148 (1992)]; however, the formation constant of the chelate has not been measured. Structure determination of rhizoferrin [Drechsel et al, 1991, supra] revealed a putrescine center symmetrically diacylated by citric acid at its 1-carboxylate:

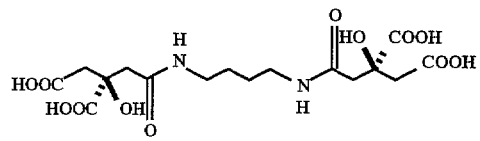

Thus, although rhizoferrin contains a polyamine backbone, it is not a member of either class of chelators. Rather, it is a hydroxy polycarboxylate, along with rhizobactin [Smith, *Tetrahedron Lett.*, Vol: 30, pages 313–316 (1989)] and staphyloferrin A [Konetschny-Rapp et al, *Eur. J. Biochem.*, Vol. 191, pages 65–74 (1990)], which are predicated on L-lysine and D-ornithine, respectively. Unlike the hydroxamates aerobactin, arthrobactin, schizokinen [Bergeron et al, "Synthesis of Catecholamide and Hydroxamate Siderophores," in *Handbook of Microbial Iron Chelators*, Winkelmann, ed., CRC Press, Inc., Boca Raton, Fla., pages 271–307 (1991)] and nannochelin [Samejima et al, *Chem. Pharm. Bull.*, Vol. 32, pages 3428–3435 (1984)], in which citric acid is symmetrically 1,3-disubstituted, the prochiral carbon of each unsymmetrically functionalized citric acid in rhizoferrin is asymmetric. These two sites of the molecule are in the (R)-configuration according to circular dichroism (CD) spectroscopy in comparison with natural (R,R)-tartaric acid [Drechsel et al, 1992, supra].

There is a need for a method for synthesizing rhizoferrin and other compounds containing a citrate moiety of desired configuration in an amide linkage. The principal challenge to such a synthesis is to access a citrate synthon of correct configuration for coupling to an amine group in order to unequivocally define the absolute configuration of the final product.

It is an object of the present invention to provide such a synthetic route.

It is another object of the invention to provide novel heavy metal chelators and pharmaceutical compositions and methods for the use thereof.

SUMMARY OF THE INVENTION

These and other objects are realized by the present invention, one embodiment of which relates to a method for synthesizing a compound of the formula:

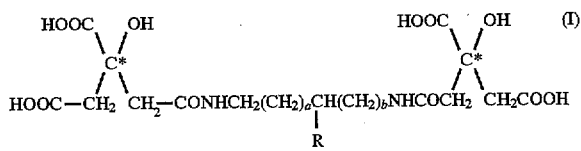

(I)

wherein:

C* is a chiral carbon atom;

a and b may be the same or different and are integers from 0 to 10, inclusive; and R is H, alkyl, arylalkyl, carboxyl or

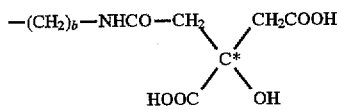

wherein C* and b have the meanings ascribed above, comprising:

(1) acylating a polyamine of the formula:

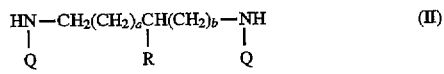

(II)

wherein:

a, b and R have the meanings ascribed above, and Q is an amine protective group, with a diester of citric acid having the formula:

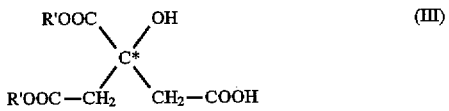

(III)

wherein:

R' is alkyl, aryl, aralkyl or cycloalkyl having up to 10 carbon atoms, to produce an amide having the formula:

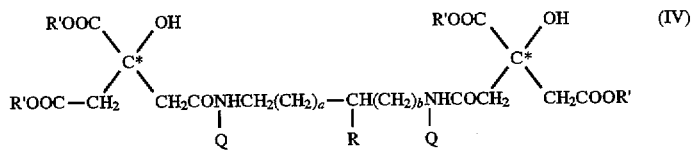

(IV)

(2) hydrolyzing the amide (IV) to produce an acid having the formula:

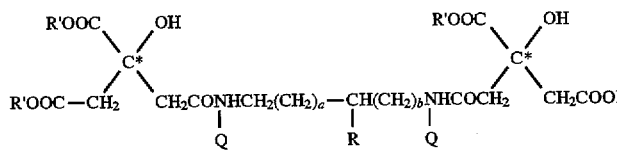

(V)

(3) deprotecting the acid (V) to remove the Q groups, thereby producing the acid of formula (I).

Another embodiment of the invention relates to certain novel heavy metal chelators having the formula:

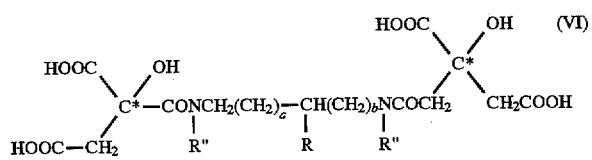

(VI)

wherein:

a, b, C* and R have the meanings ascribed above and R" is R' or Q, and salts thereof with pharmaceutically acceptable acids and cations.

An additional embodiment of the invention relates to pharmaceutical compositions in unit dosage form comprising a therapeutically effective amount of a compound of formula VI or a salt thereof with a pharmaceutically acceptable acid or cation and a pharmaceutically acceptable carrier therefor.

A further embodiment of the invention relates to methods for the treatment of human and non-human mammals in need thereof comprising the administration thereto of a therapeutically effective amount of a compound of formula VI or a salt thereof with a pharmaceutically acceptable acid or cation.

DETAILED DESCRIPTION OF THE INVENTION

The invention will be described in detail with reference to the synthesis of rhizoferrin; it being understood by those skilled in the art that the principles of the invention as broadly described herein are applicable to the preparation of any compound embodying a citric acid moiety of particular enantiomeric configuration coupled via an amide linkage to an amine.

The synthetic scheme for preparing rhizoferrin is as follows:

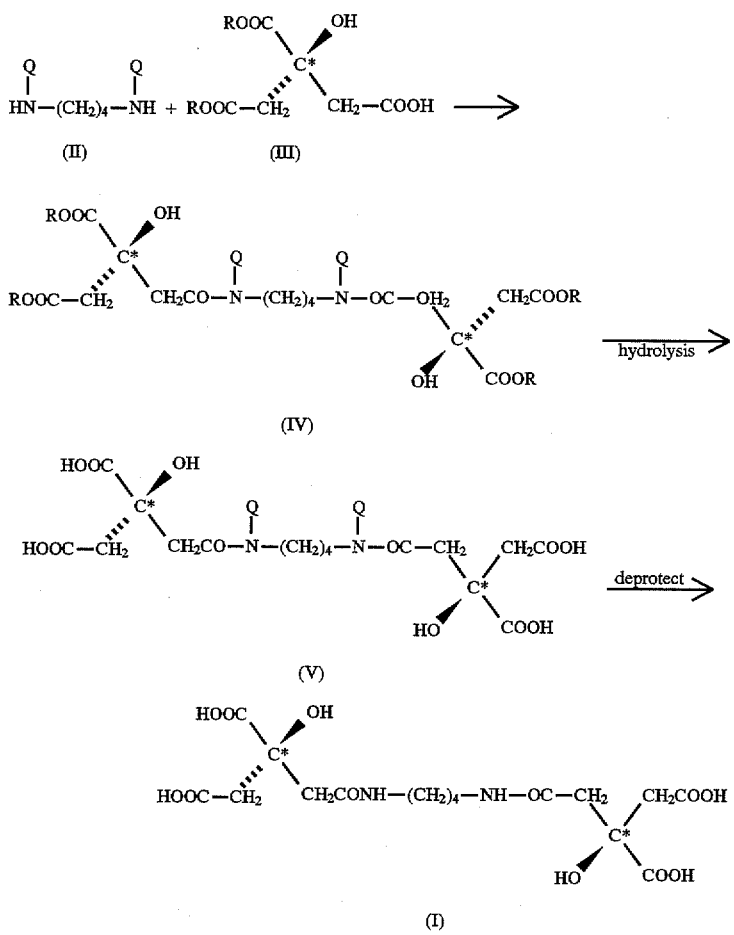

The enantiomer (III) may be accessed via the following scheme:

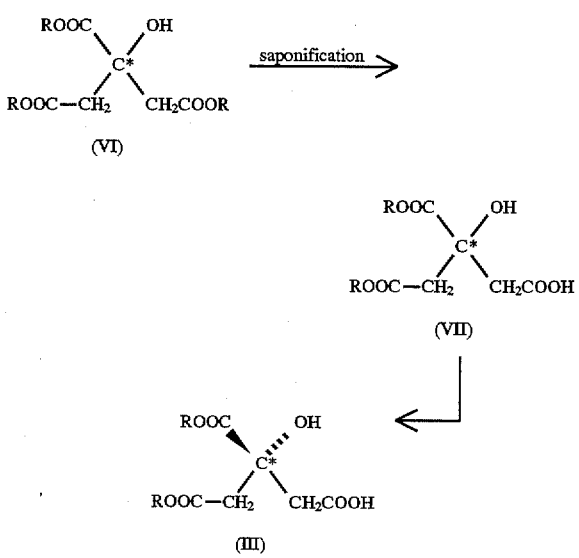

In the above structural formulae and schemes, R may be the residue of any suitable esterifying alcohol having up to 10 carbon atoms such as alkyl (e.g., methyl, ethyl, propyl, butyl); aryl (e.g., phenyl); aralkyl (e.g., benzyl) or cycloalkyl (e.g., cyclopentyl, cyclobenzyl).

The diamine reactant may be any suitable amine containing primary amine groups such as those of formula (II). Therein R may be alkyl, aryl, aralkyl or cycloalkyl, each having up to 10 carbon atoms or

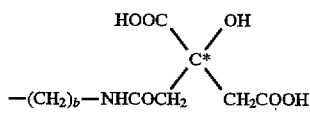

The expression "amino protective group" (Q) as used herein is intended to designate the Q group which is inserted in place of a hydrogen atom of an amino group or groups in order to protect the amino group(s) during synthesis.

Selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, by Bodanszky in *Principles of Synthesis*, Springer-Verlag, New York (1984); by Ives in U.S. Pat. No. 4,619,915; and in the various publications referred to in the latter. See also *Methoden der Organischen Chemie*, Houben-Weyl, Vol. 15, No. 1, for protecting groups and Vol. 15, No. 2, for methods of peptide synthesis. Representative amino protecting groups for synthetic use include benzyl and acyl groups such as tert-butoxycarbonyl, benzyloxycarbonyl, benzoyl, acetyl and the like. Yet other conventional amino protecting groups for use in synthesis are described in the literature [Bodanszky, supra, and Ives, supra].

The synthesis of rhizoferrin typically begins with trimethyl citrate which is converted to 1,2-dimethyl citrate by a sterically controlled saponification [Hirota et al, *Chemistry Lett.*, pages 191–194 (1980)]. The enantiomers of the carboxylic acid are separated by forming their (−)-brucine salts. After five fractional crystallizations from water, the crystalline salt is shown by single crystal X-ray diffraction to contain 1,2-dimethyl citrate in the (R)-configuration. Treatment of the salt with 1N HCl and extraction with ethyl acetate furnishes (R)-1,2-dimethyl citrate.

With the correct enantiomeric acid in hand, $N^1,N^4$-dibenzyl-1,4-diaminobutane [Samejima et al, supra] was acylated with (R)-1,2-dimethyl citrate (2 equivalents) utilizing diphenylphosphoryl azide ($Et_3N/DMF$) [Shioiri et al, *J. Am. Chem. Soc.*, Vol. 94, pages 6203–6205 (1972)]. The diamide was obtained in 26% yield after flash column chromatography, which removed by-products including olefins due to elimination of the tertiary alcohol as indicated by NMR. The methyl esters were hydrolyzed with sodium hydroxide in aqueous methanol and acidification gave N,N'-dibenzyl rhizoferrin.

Finally, since N-benzyl amides are resistant to hydrogenolysis [Williams et al, *Tetrahedron Lett.*, Vol. 30, pages 451–454 (1989)], deprotection of the tetraacid under dissolving metal reduction conditions ($Li/NH_3/THF$) [Kim et al, *J. Org. Chem.*, Vol. 46, pages 5383–5389 (1981)], protonation of the salts on a cation exchange resin column and purification on a C-18 reversed-phase column furnished the final product, rhizoferrin. The high field NMR and high resolution mass spectrum of the synthetic compound were essentially identical to the published spectra of the natural product [Drechsel et al, 1991, supra]. The absolute configurations (R, R) of the synthetic sample and the natural material are identical since both exhibited a negative Cotton effect at the same wavelength [Drechsel et al, 1992, supra].

Rhizoferrin cyclizes upon standing through dehydration to imidorhizoferrin and bis-imidorhizoferrin which possess one and two five-membered rings, respectively [Drechsel et al, 1992, supra]. It was observed by NMR that the zero order rate constant for this ring formation at pH 5.0 is $6.9 \times 10^{-2}$ $h^{-1}$. At pH 3, the findings on the extent of cyclization were similar to the literature [Drechsel et al, 1992, supra]; thus the analytical data were obtained before this decomposition occurred.

This synthetic methodology for rhizoferrin may also be used to prepare the hydroxy polycarboxylated siderophore staphyloferrin A [Konetschny-Rapp et al, supra; and Meiwes et al, *FEMS Microbiol. Lett.*, Vol. 67, pages 201–206 (1990)], in which D-ornithine is $N^\alpha,N^\delta$-diacylated with citric acid at its 1-carboxylate. In addition, analogues of rhizoferrin in which the chain length of the central methylene bridge is varied can be synthesized for structure-activity studies.

The compounds of formula VI, useful as heavy metal chelators, are prepared in the same manner as those of formula V.

The pharmaceutical compositions of the invention preferably contain a pharmaceutically acceptable carrier suitable for rendering the compound or mixture administrable orally as a tablet, capsule or pill, or parenterally or transdermally. The active ingredients may be admixed or compounded with any conventional, pharmaceutically acceptable carrier. It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in *Remington's Pharmaceutical Sciences*, 4th ed. (1970), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

The therapeutically effective amount of active agent to be included in the pharmaceutical composition of the invention depends, in each case, upon several factors, e.g., the type, size and condition of the patient, the disorder to be treated, the intended mode of administration, the capacity of the patient to incorporate the intended dosage form, etc. Generally, an amount of active agent is included in each dosage form to provide from about 50 to about 500 mg, preferably from about 50 to about 250 mg.

The active agent employed in the pharmaceutical compositions and methods of treatment of the invention may comprise a pharmaceutically acceptable salt or complex of the compounds of formula I or II, e.g., sodium, potassium or other non-toxic metal salts, amine salts, etc., as well as acid salts with, e.g., HCl, HAc, etc.

The compound, compositions and method of the invention are useful for the treatment of heavy metal, e.g., iron, overload diseases such as thalassemia.

Those skilled in the art will be aware that the amounts of the various components of the compositions of the invention to be administered in accordance with the method of the invention to a patient will depend upon those factors noted above. Generally, however, amounts of active agent are administered to provide dosages thereof from about 50 to about 500 mg/kg, preferably from about 50 to about 250 mg/kg, the frequency of administration and duration of treatment being dependent upon the type and nature of the patient and disorder being treated.

The invention is illustrated by the following non-limiting examples, wherein silica gel 32–63 (40 μm "flash") or silica gel 60 (70–230 mesh) was used for column chromatography. Optical rotations were run in $CH_3OH$ at 589 nm (Na lamp) at room temperature with c as grams of compound per 100 ml. $^1H$ NMR spectra were recorded at 300 or 600 MHz and run in the deuterated organic solvent indicated or in $D_2O$ with chemical shifts given in parts per million downfield from tetramethylsilane or 3-(trimethylsilyl)propionic-2,2,3,3-$d_4$ acid, sodium salt, respectively. X-ray diffraction data were collected at 173K on a Siemens SMART PLATFORM equipped with a CCD area detector and a graphite monochromator utilizing $MoK_\alpha$ radiation ($\lambda=0.71073$ Å). Cell parameters were refined using up to 6233 reflections. A hemisphere of data (1381 frames) was collected using the ω-scan method (0.3° frame width). The first 50 frames were remeasured at the end of data collection to monitor instrument and crystal stability (maximum correction on I was <1%). Psi scan absorption corrections were applied based on the entire data set.

Circular dichroism spectra were obtained with a Jasco Model J500C spectropolarimeter equipped with a Jasco IF-500II interface and CompuAdd 286 computer; data collection and processing were performed with Jasco DP-500/PC System version 1.28 software. The cell path length was 2.00 cm.

Ultraviolet spectroscopy spectra were obtained with a Shimadzu UV-2501PC equipped with an AST 486/33 computer data station. The cell path length was 1.00 cm.

EXAMPLE 1

1,2-Dimethyl citrate (2) was prepared by modification of a published method [Hirota et al, supra]. Sodium hydroxide (0.1N, 215 ml) was added to a solution of trimethyl citrate (1) (10.0 g, 42.7 mmol) in 50% aqueous ($CH_3OH$ (200 ml) over 2 hours with vigorous stirring at room temperature. The solution was concentrated to about 150 ml and extracted with EtOAc (3×150 ml). The aqueous layer was acidified with 1N HCl (45 ml) and extracted with EtOAc (3×150 ml). The organic layer was dried ($MgSO_4$) and concentrated, providing 3.70 g (39%) of (2) was a colorless oil: $^1H$ NMR ($d_6$-DMSO) δ 5.60 (br s, 1H, OH), 3.64 (s, 3H, $CO_2CH_3$), 3.57 (s, 3H, $CO_2CH_3$), 2.87 (d, 1H, J=15 Hz, ½ $CH_2$), 2.81 (d, 1H, J=15 Hz, ½ $CH_2$), 2.65 (d, 1H, J=15 Hz, ½ $CH_2$).

EXAMPLE 2

1,2-Dimethyl-3-[(S)-sec-phenethyl] citrate (3) was prepared by adding 1,3-dicyclohexylcarbodiimide (103 mg, 0.5 mmol) to a solution of (2) (110 mg, 0.5 mmol), (S)-(−)-sec-phenethyl alcohol (61 mg, 0.5 mmol) and 4-dimethylaminopyridine (3 mg) in dry $CH_2Cl_2$ (10 ml) at 0° C., and the mixture was stirred overnight. The mixture was filtered and the filtrate was concentrated and purified by flash chromatography (1:2 EtOAc/hexane), resulting in 60 mg (37%) of (3) as a colorless oil: $^1H$ NMR ($CDCl_3$) δ 7.35–7.28 (m, Ph), 5.97 (q, J=7 Hz, CHPh), 5.88 (q, J=7 Hz, CHPh), 3.77 (s, $CH_3O$), 3.73 (s, $CH_3O$), 3.69 (s, $CH_3O$), 3.68 (s, $CH_3O$), 2.98–2.74 (m, $CH_2$), 1.54 (d, J=7 Hz, C—$CH_3$), 1.52 (d, J=7 Hz, C—$CH_3$).

EXAMPLE 3

(−)-Brucine salt of (R)-1,2-dimethyl citrate was prepared by adding (2) (7 g, 31.8 mmol) to a solution of (−)-brucine (12.5 g, 31.8 mmol) (CAUTION: toxic) in EtOAc (460 ml) with vigorous stirring overnight. After filtration, the precipitate (10.5 g) was recrystallized from water (5×) and dried to afford 2.04 g of white crystals: mp 165°–168° C.

The diastereomeric salt crystallizes in the monoclinic space group C2 and has cell dimensions: a=13.8947 (3), b=12.4224 (3), and c=17.5408 (3) Å; α=90°, β=104.556 (1), and δ=90°. The structure was solved by the Direct Methods in SHELXTL [Sheldrick, *SHELXTL*, Siemens XRD Corporation, Madison, Wis. (1995)] and was refined using full matrix least squares. The non-H atoms were treated anisotropically. The methyl hydrogen atoms were calculated in ideal positions and were riding on their respective carbon atoms; the rest of the H atoms were refined without constraints. Two water molecules were located in the asymmetric unit. One was refined with full occupancy and its H atoms were located. The other water molecule, located on a 2-fold axis of rotation, was refined to a 30% occupancy. An absolute configuration of (R) was assigned to the citrate portion of the salt based on knowledge of the stereochemistry of brucine. Parameters (521) were refined in the final cycle of refinement using 3855 reflections with I>2 ρ (I) to yield $R_1$ and $wR_2$ of 0.0434 and 0.1040, respectively. Refinement was conducted using $F^2$.

EXAMPLE 4

(R)-1,2-Dimethyl citrate (4). HCl (1N, 4 ml) was added to a solution of the (−)-brucine salt of (R)-1,2-dimethyl citrate (2.04 g, 3.32 mmol) in water (50 ml) and stirring was continued for 5 minutes. Extraction with EtOAc (3×50 ml), drying over $Na_2SO_4$ and concentration gave 630 mg (86%) of (4) as a colorless oil: [α] +4.0 (c 1.00); the NMR was identical to (2).

EXAMPLE 5

N,N'-Dibenzyl rhizoferrin, tetraethyl ester (6). Diphenylphosphoryl azide (760 mg, 2.76 mmol) and $NEt_3$ (1.5 ml, 11 mmol) were added to a solution of (4) (610 mg, 2.77 mmol) and $N^1,N^4$-dibenzyl-1,4-diaminobutane [Samejima et al, supra] (370 mg, 1.38 mmol) in DMF (20 ml) at 0° C. under nitrogen. The solution was stirred at 0° C. for 1 hour and then at room temperature for 23 hours. After solvents were removed under high vacuum, the residue was taken up in EtOAc (25 ml) and was washed with saturated $NaHCO_3$ (25 ml), water (25 ml), 0.5N HCl (25 ml) and water (25 ml). The organic layer was dried ($MgSO_4$) and concentrated. Flash chromatography, eluting with 4:1 EtOAc/hexane, generated 240 mg (26%) of (6) as a pale yellow oil: [α] +8.25 (c 1.00); $^1H$ NMR ($CDCl_3$) δ 7.42–7.24 (m, 10H), 4.65–4.48 (m, 4H), 3.81 (s, 3H, $OCH_3$), 3.79 (s, 3H, $OCH_3$), 3.69 (s, 3H, $OCH_3$), 3.65 (s, 3H, $OCH_3$), 3.40–3.12 (m, 4H), 3.10–2.67 (m, 8H), 1.57–1.41 (m, 4H). Anal. calcd. for $C_{34}H_{44}N_2O_{12}$: C 60.70, H 6.59, N 4.16. Found: C 60.64, H 6.61, N 4.15.

EXAMPLE 6

N,N'-Dibenzyl rhizoferrin (7). A solution of (6) (170 mg, 0.253 mmol) in $CH_3OH$ (7 ml) and 1N NaOH (7 ml) was stirred at room temperature for 5 hours. HCl (1N, 8 ml) was added and the solution was concentrated to about 15 ml. After extraction with EtOAc (3×15 ml), the organic layer was dried ($Na_2SO_4$) and concentrated to give 120 mg (77%) of (7) as a colorless glass: [α] +12.27 (c 1.00); $^1H$ NMR ($CD_3OD$) δ 7.42–7.20 (m, 10H, 2 Ph), 4.67–4.47 (m, 4H, $CH_2Ph$), 3.35–3.23 (m, 4H, 2 $NCH_2$), 3.19–2.69 (m, 8H, 4 $CH_2CO$), 1.58–1.41 (m, 4H, 2 $CH_2$). Anal. calcd. for $C_{30}H_{36}N_2O_{12} \cdot H_2O$: C 56.78, H 6.04, N 4.41. Found: C 56.88, H 6.08, N 4.34.

EXAMPLE 7

Rhizoferrin. A solution of (7) (110 mg, 0.178 mmol) in distilled THF (1.5 ml) was added to Li (33 mg, 4.8 mmol) in $NH_3$ (100 ml) and the mixture was maintained at −78° C. for 3 hours. Aqueous $H_3OH$ (50%, 10 ml) was added until the blue color disappeared. Ammonia was evaporated and the residue was taken up in water (50 ml) through a cation exchange resin column (Bio Rad, AG 50W-X8). The eluant containing product (pH=3) was extracted with EtOAc (50 ml) which was concentrated to dryness. The residue was dissolved in distilled EtOH (2 ml), filtered and concentrated to yield 50 mg (64%) of rhizoferrin as a colorless glass: HRMS (FAB, m-nitrobenzyl alcohol matrix) calcd. for $C_{16}H_{25}N_2O_{12}$ 437.1407 (M+H), found 437.1407 (base). Anal. calcd. for $C_{16}H_{24}N_2O_{12} \cdot H_2O$: C 42.29, H 5.77, N 6.17. Found: C 42.49, H 5.80, N 5.84.

A solution of crude product (10 mg) was purified by reversed-phase HPLC [Drechsel et al, 1992, supra] (C-18 preparative column, 21.4 mm×25 cm, obtained from Rainin). The initial mobile phase concentration of 3% $CH_3CN$ in 0.1% TFA was held for 15 minutes, followed by gradient elution of 3–11% $CH_3CN$ in 0.1% TFA over 35 minutes, then held at 11% $CH_3CN$ in 0.1% TFA for 20 minutes. Flow rate was maintained at 4 ml per minute. Retention time was 56 minutes. Lyophilization gave 4.32 mg (9.90 μmol) of purified rhizoferrin as a colorless glass: [α] −16.7 (26° C.) (c 0.1613); $^1H$ NMR ($D_2O$) δ 3.21–3.15 (m, 4H), 3.02 (d, 2H, J=16.0 Hz), 2.79 (d, 2H, J=16.0 Hz), 2.76 (d, 2H, J=14.6 Hz), 2.65 (d, 2H, J=14.6 Hz), 1.53–1.47 (m, 4H).

A stock solution was prepared by dissolving the purified product in 50.00 ml distilled water; a 10.00 ml aliquot was diluted to 20.00 ml and adjusted to pH=3.02 with 1.90 ml of 0.010N HCl (final rhizoferrin concentration=$9.04 \times 10^{-5}$M). CD and UV spectra were taken immediately after pH adjustment. All spectra were baseline corrected with a distilled water blank which was acidified as above.

CD Results

The CD spectra of rhizoferrin exhibited a negative Cotton effect from 200 to 220 nm, with a single minimum at 205 nm, $\Delta\epsilon=-2.7$ compared to a recorded single minimum [Drechsel et al, 1992, supra] at 204 nm, $\Delta\epsilon=-4.3$.

| UV Results | | |
|---|---|---|
| nm | $\epsilon$ | $\epsilon^{10}$ |
| 196 | 12200 | (13900) |
| 200 | 10800 | (13150) |
| 210 | 5230 | (5600) |
| 215 | 2770 | (3000) |
| 220 | 1200 | (1400) |

I claim:

1. A method for synthesizing a compound of the formula:

$$\text{HOOC}\diagdown_{C^*}\diagup\text{OH} \qquad \text{HOOC}\diagdown_{C^*}\diagup\text{OH} \qquad (I)$$
$$\text{HOOC}-\text{CH}_2 \quad \text{CH}_2-\text{CONHCH}_2(\text{CH}_2)_a\text{CH}(\text{CH}_2)_b\text{NHCOCH}_2 \quad \text{CH}_2\text{COOH}$$
$$\hspace{6cm} | \hspace{1cm} R$$

wherein:

C* is a chiral carbon atom;

a and b may be the same or different and are integers from 0 to 10, inclusive; and R is H, alkyl, arylalkyl, carboxyl or $$-(\text{CH}_2)_b-\text{NHCO}-\text{CH}_2\diagdown_{C^*}\diagup\text{CH}_2\text{COOH}$$
$$\hspace{3cm}\text{HOOC}\diagup\hspace{0.2cm}\diagdown\text{OH}$$

wherein C* and b have the meanings ascribed above, comprising:

(1) acylating a polyamine of the formula:

$$\text{HN}-\text{CH}_2(\text{Ch}_2)_a\text{CH}(\text{CH}_2)_b-\text{NH} \qquad (II)$$
$$| \hspace{2cm} | \hspace{2cm} |$$
$$Q \hspace{2cm} R \hspace{2cm} Q$$

wherein:

a, b and R have the meanings ascribed above, and Q is an amine protective group, with a diester of citric acid having the formula:

$$\text{R'OOC}\diagdown_{C^*}\diagup\text{OH} \qquad (III)$$
$$\text{R'OOC}-\text{CH}_2 \quad \text{CH}_2-\text{COOH}$$

wherein:

R' is alkyl, aryl, aralkyl or cycloalkyl having up to 10 carbon atoms, to produce an amide having the formula:

$$\text{R'OOC}\diagdown_{C^*}\diagup\text{OH} \qquad \text{R'OOC}\diagdown_{C^*}\diagup\text{OH} \qquad (IV)$$
$$\text{R'OOC}-\text{CH}_2 \quad \text{CH}_2\text{CONHCH}_2(\text{CH}_2)_a-\text{CH}(\text{CH}_2)_b\text{NHCOCH}_2 \quad \text{CH}_2\text{COOR'}$$
$$\hspace{6cm} | \hspace{1cm} | \hspace{1cm} |$$
$$\hspace{6cm} Q \hspace{1cm} R \hspace{1cm} Q$$

(2) hydrolyzing amide (IV) to produce an acid having the formula:

$$\text{HOOC}\diagdown_{C^*}\diagup\text{OH} \qquad \text{HOOC}\diagdown_{C^*}\diagup\text{OH} \qquad (V)$$
$$\text{HOOC}-\text{CH}_2 \quad \text{CH}_2-\text{CONHCH}_2(\text{CH}_2)_a\text{CH}(\text{CH}_2)_b\text{NHCOCH}_2 \quad \text{CH}_2\text{COOH}$$
$$\hspace{6cm} | \hspace{1cm} | \hspace{1cm} |$$
$$\hspace{6cm} Q \hspace{1cm} R \hspace{1cm} Q$$

(3) deprotecting acid (V) to remove the Q groups, thereby producing an acid of formula (I).

2. The method of claim 1 wherein a=1, b=1 and R=H.

3. The method of claim 2 wherein said polyamine is an aliphatic diamine.

4. The method of claim 3 wherein said aliphatic diamine is 1,4-diaminobutane.

5. The method of claim 1 wherein Q is a benzyl group.

6. The method of claim 1 wherein R is methyl.

7. The method of claim 1 wherein said diester of citric acid (III) is a racemic mixture thereof.

8. The method of claim 1 wherein said diester of citric acid (III) is an enantiomer thereof.

9. The method of claim 8 wherein said diester of citric acid (III) is an (R) enantiomer.

10. The method of claim 9 wherein said polyamine is 1,4-diaminobutane and said compound (I) is rhizoferrin.

11. A method of synthesizing rhizoferrin comprising acylating $N^1,N^4$-dibenzyl-1,4-diaminobutane with (R)-1,2-dimethyl citrate to produce a compound of the formula:

$$\text{H}_3\text{COOC}\diagdown_{C^*}\diagup\text{OH} \qquad\qquad\qquad \text{CH}_2\text{C}_6\text{H}_5 \qquad\qquad\qquad (VII)$$
$$\text{H}_3\text{COOC}-\text{CH}_2 \quad \text{CH}_2-\text{CO}-\text{N}-(\text{CH}_2)_4-\text{N}-\text{OC}-\text{CH}_2 \quad \text{CH}_2-\text{COOCH}_3$$
$$\hspace{5cm} | \hspace{4cm} \diagdown_{C}\diagup$$
$$\hspace{5cm} \text{CH}_2\text{C}_6\text{H}_5 \hspace{3cm} \text{HO}\diagup\hspace{0.2cm}\diagdown\text{COOCH}_3$$

hydrolyzing formula (VII) to produce the acid of the formula:

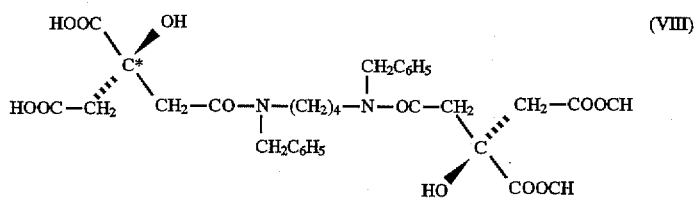

(VIII)

and debenzylating formula (VIII) to produce rhizoferrin.

12. The method of claim 11 wherein said acylation is effected utilizing diphenylphosphoryl azide and triethylamine.

13. The method of claim 12 wherein said acylation is effected in a solvent comprising dimethyl formamide.

14. The method of claim 11 wherein said hydrolysis of formula (VII) to produce formula (VIII) is effected in alkaline methanol.

15. The method of claim 11 wherein said debenzylation of formula (VIII) to produce rhizoferrin is effected under dissolving metal reduction conditions.

16. The method of claim 15 wherein said dissolving metal reduction conditions comprise Li in $NH_3$.

17. The method of claim 1 including the step of preparing the citric acid diester (III) by the sterically controlled saponification of a citric acid triester having the formula:

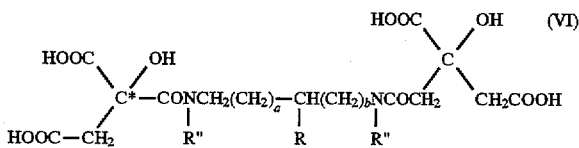

wherein:

a, b, C* and R have the meanings ascribed above and R" is R' or Q, and salts thereof with pharmaceutically acceptable acids and cations.

18. The method of claim 17 wherein R is methyl and said sterically controlled saponification of formula (VI) is effected in an alkaline solution of methyl alcohol.

19. The method of claim 18 including the step of preparing the enantiomer of said citric acid diester (III).

20. The method of claim 19 wherein said enantiomer is prepared by separating the enantiomers of a racemic mixture of said citric acid diester (III).

21. The method of claim 20 wherein said racemic mixture is separated to produce said enantiomer by reacting the mixture with a chiralic base to produce a diastereoisomeric salt.

* * * * *

UNITED STATES PATENT AND TRADEMARK OFFICE
CERTIFICATE OF CORRECTION

PATENT NO. : 5,739,395
DATED : April 14, 1998
INVENTOR(S) : Raymond J. BERGERON, JR.

Page 1 of 2

It is certified that error appears in the above-indentified patent and that said Letters Patent is hereby corrected as shown below:

In Column 11, line 46: delete the formula and substitute the following:

In Column 12, line 22: delete the formula and substitute the following:

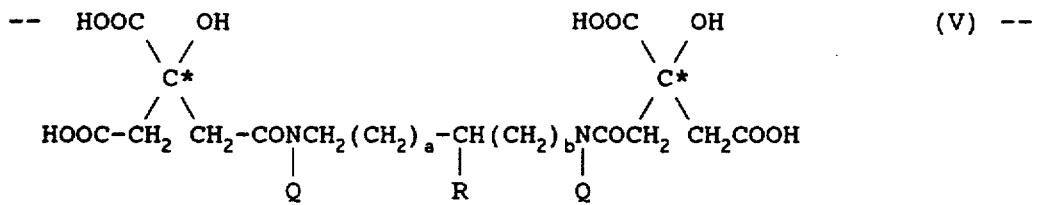

In Column 12, line 51: delete the formula and substitute the following:

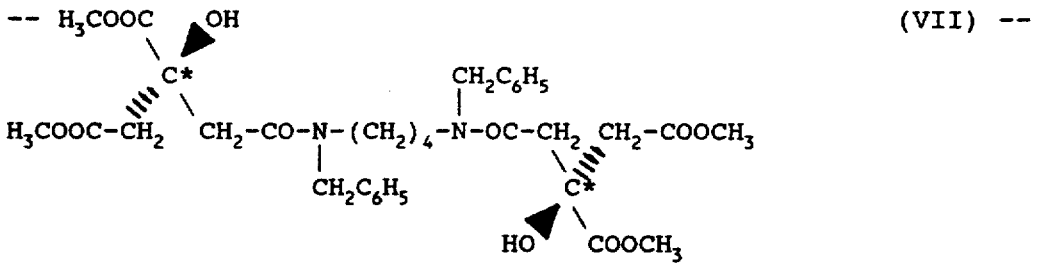

UNITED STATES PATENT AND TRADEMARK OFFICE
CERTIFICATE OF CORRECTION

PATENT NO. : 5,739,395
DATED : April 14, 1998
INVENTOR(S) : Raymond J. BERGERON, JR.

It is certified that error appears in the above-indentified patent and that said Letters Patent is hereby corrected as shown below:

In Column 13, line 1: delete the formula and substitute the following:

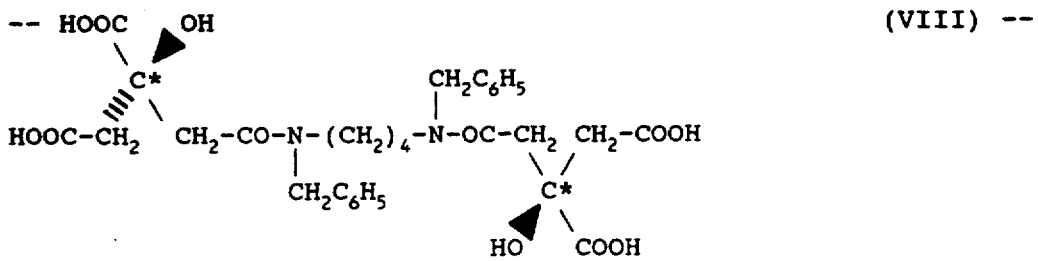

In Column 13, line 27: delete the formula and substitute the following:

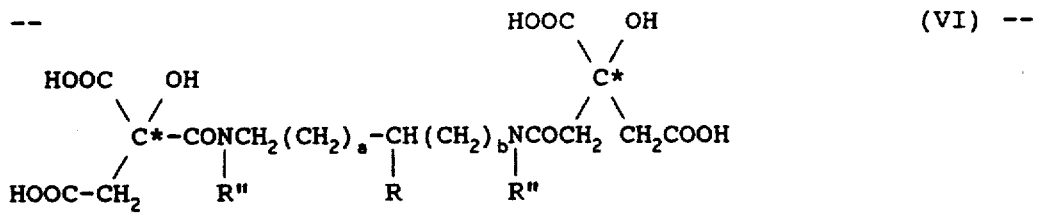

Signed and Sealed this

Fourteenth Day of July, 1998

*Attest:*

BRUCE LEHMAN

*Attesting Officer*     *Commissioner of Patents and Trademarks*